(12) United States Patent
Finke (10) Patent No.: US 11,096,805 B2
(45) Date of Patent: Aug. 24, 2021

(54) LINER FOR A PROSTHESIS

(71) Applicant: Ottobock SE & Co. KGaA, Duderstadt (DE)

(72) Inventor: Lars Benjamin Finke, Landolfshausen (DE)

(73) Assignee: OTTOBOCK SE & CO. KGAA

( * ) Notice: Subject to any disclaimer, the term of this patent is extended or adjusted under 35 U.S.C. 154(b) by 0 days.

(21) Appl. No.: 16/499,811

(22) PCT Filed: Mar. 19, 2018

(86) PCT No.: PCT/EP2018/056814
§ 371 (c)(1),
(2) Date: Sep. 30, 2019

(87) PCT Pub. No.: WO2018/177783
PCT Pub. Date: Oct. 4, 2018

(65) Prior Publication Data
US 2020/0100920 A1     Apr. 2, 2020

(30) Foreign Application Priority Data

Mar. 30, 2017   (DE) .......................... 102017106903.8

(51) Int. Cl.
| | |
|---|---|
| *B33Y 70/00* | (2020.01) |
| *A61F 2/80* | (2006.01) |
| *A61F 2/78* | (2006.01) |
| *A61F 2/50* | (2006.01) |

(52) U.S. Cl.
CPC .......... *A61F 2/7812* (2013.01); *A61F 2/5044* (2013.01); *A61F 2002/5026* (2013.01); *A61F 2002/5055* (2013.01)

(58) Field of Classification Search
CPC .................. A61F 2/7812; A61F 2/5044; A61F 2002/5026; A61F 2002/5055; A61F 2002/7818; A61F 2002/7875; A61F 2002/7881; A61F 2/80; B33Y 70/00
See application file for complete search history.

(56) References Cited

U.S. PATENT DOCUMENTS

| | | | |
|---|---|---|---|
| 9,486,333 B2 | 11/2016 | Wang et al. | |
| 2005/0101693 A1* | 5/2005 | Arbogast | A61F 2/7812 523/122 |
| 2010/0070051 A1* | 3/2010 | Carstens | A61F 2/80 623/34 |

(Continued)

FOREIGN PATENT DOCUMENTS

| | | |
|---|---|---|
| DE | 10153796 A1 | 6/2003 |
| DE | 102012017324 A1 | 3/2014 |

(Continued)

*Primary Examiner* — Jennifer Dieterle
*Assistant Examiner* — Mihret Tafesse
(74) *Attorney, Agent, or Firm* — Holland & Hart LLP (57) ABSTRACT

A liner for a prosthesis, wherein the liner is made of a liner material and comprises a proximal opening for accommodating an amputation stump, a distal end, a longitudinal direction, which extends from the proximal opening to the distal end, and an auxetic material The auxetic material is a two-dimensional-auxetic material, which is arranged in such a way that an extension of the liner in the longitudinal direction leads to an expansion of a diameter of the liner.

18 Claims, 5 Drawing Sheets

(56) References Cited

U.S. PATENT DOCUMENTS

2013/0274896 A1\* 10/2013 Wang ................ A61F 7/007
 623/36
2016/0318255 A1\* 11/2016 Ou ................... B29C 64/386

FOREIGN PATENT DOCUMENTS

DE     102012022484 A1    5/2014
EP         1165865 B1    7/2005

\* cited by examiner

LINER FOR A PROSTHESIS

CROSS REFERENCE TO RELATED APPLICATIONS

This application is a U.S. National Entry and claims priority to PCT International Patent Application No. PCT/EP2018/056814, filed 19 Mar. 2018, and entitled "LINER FOR A PROSTHESIS", which claims priority to European Patent Application No. 102017106903.8 filed 30 Mar. 2017, the entire disclosures of which are incorporated herein by this reference.

TECHNICAL FIELD

The invention relates to a liner for a prosthesis, wherein the liner is made of a liner material and comprises a proximal opening for accommodating an amputation stump, a distal end and a longitudinal direction that extends from the proximal opening to the distal end and comprises an auxetic material.

BACKGROUND

This type of liner has been known within the scope of the prior art for many years and is pulled over an amputation stump before it is inserted into a prosthetic socket. Here, the liner may perform various tasks.

SUMMARY

It is common to hold the prosthetic socket on the amputation stump by extracting air from a volume between the prosthetic socket and the liner that is pulled over the amputation stump. In this case, the prosthesis is held on the amputation stump solely by the vacuum present in the volume. To achieve this, it is of course necessary for the volume to be sealed such that it is airtight; specifically, this requires that the proximal edge of the prosthetic socket lie flat on the liner such that it is airtight. The disadvantage of this type of treatment is that the system is complex and its operation intricate and difficult.

As an alternative to this vacuum solution, it is therefore possible to provide a mechanical fixing device at the distal end of the liner, such as a pin or a similar device, by means of which the liner can be arranged on a correspondingly configured counterpiece on the inside of the prosthetic socket. In this case, there is no need for a vacuum between the prosthetic socket and the prosthetic liner; either that, or it is used as a support at most.

When walking, a force acting in the distal direction occurs during the swing phase of each step; as a result, the prosthetic socket pulls on the amputation stump. A force is thus exerted which acts along the longitudinal direction of the liner. In particular, with regards to liners that are mechanically fixed to the distal end on the inside of the prosthetic socket, said distally acting tensile force is transferred directly to the liner, said tensile force trying to effect an elongation of the liner along its longitudinal direction. If the liner is made of silicon, for example, or another elastic material, such an elongation in the longitudinal direction leads to a reduction in the circumference, causing the so-called "milking effect", which is unpleasant and should be avoided, Furthermore, amputation stumps tend to change their volume, for instance over the course of a day. A liner that is made exclusively of an elastic material can follow such a change in volume, for instance by way of a decrease in the elastic expansion of the liner material upon a reduction in volume, thereby enabling the circumference of the liner to follow the shrinking circumference of the amputation stump. In the same way, the elastic liner can expand further if the volume of the amputation stump increases over the course of the day, provided that the rigid prosthetic socket surrounding the liner allows as such.

A range of approaches are known from the prior art, to react to such changes in volume. For instance, DE 10 2012 017 324 A1 describes the insertion of inelastic fibers in the elastic liner material, which results in an extension in the liner along its longitudinal direction and a shortening in the circumferential direction and vice-versa. In the event of an increase in volume, the circumference should therefore become larger, which would also result in a shortening of the liner in the longitudinal direction. To this end, the liner would have to slide along the skin of the wearer, which is not possible due to the adhesive properties. As far as possible, this should prevent any changes in volume.

U.S. Pat. No. 9,486,333 B2 proposes a different approach. Here, a three-dimensional-auxetic material is used inside the liner, said material being designed as an auxetic foam. Auxetic materials have negative Poisson's ratios. This means that, unlike with conventional materials, an extension of the material in one direction does not lead to a shortening in a respective other direction; rather, an extension also occurs in these directions. As a result, the three-dimensional-auxetic material from the prior art stretches if the volume of the liner shrinks. In this case, it is necessary for the material to be connected to the amputation stump and the inner side of the prosthetic socket in such a way that it does not become detached upon a reduction in the volume of the amputation stump. It can thus react to the increase in the distance between the amputation stump and prosthetic socket and, thanks to its three-dimensional-auxetic nature, fill the resulting space. This should guarantee a secure hold on the prosthetic socket, even on an amputation stump that is reducing in size. However, it is impractical that the three-dimensional-auxetic material also expands when a force is acting in another direction, for example during the swing phase of a gait cycle. The auxetic material thus tends to expand during the swing phase as well, thereby intensifying the milking effect and forcing a reduction in the volume of the amputation stump.

US 2005/0101693 A1 describes a liner that exhibits different degrees of elasticity in different regions and, in particular, that may be impregnated or coated with a polymer gel.

The invention aims to improve a liner according to the present disclosure in such a way that the disadvantages named are avoided or at least mitigated.

The invention solves the task at hand by way of a liner having a two dimensional-auxetic material, which is arranged in such a way that an extension of the liner in the longitudinal direction leads to an increase of a diameter of the liner.

Two-dimensional-auxetic materials and methods for their production are described in EP 1 165 865 B1, for example. Auxetic materials have a negative transverse strain or a negative Poisson's ratio. In two-dimensional-auxetic materials, when a tensile force is acting the expansion of the material increases in a first direction as well as in a second direction that is, for example, perpendicular to the first direction, without a significant change in the expansion in the third perpendicular direction. It is preferable if no change occurs in this third direction.

In particular, during a swing phase of a gait cycle, tensile forces acting in the longitudinal direction occur, as previously explained, said tensile forces acting on the liner for the prosthesis. In this case, due to the two-dimensional-auxetic properties, an expansion of the diameter of the liner occurs, such that the acting tensile forces that are transferred to the amputation stump act not only along the longitudinal direction, but also especially in the radial direction. On the one hand, this results in an as homogeneous as possible distribution of the acting forces and, on the other hand, causes changes in volume, especially a reduction in volume, to be actively countered. With the liner according to the invention, it is not necessary to fill a gap, which develops between a shrinking amputation stump and the prosthetic socket, with an expanding three-dimensional-auxetic material, since the two-dimensional-auxetic material used counters this reduction in volume in the amputation stump. An expansion of the two-dimensional-auxetic material in the radial direction in relation to the longitudinal direction, i.e. an increase in the thickness of the liner, does not occur according to the invention.

The liner preferably has a fixing element, preferably a positive-locking element, in particular a pin, with which said liner can be introduced in a recess of the prosthetic socket and thus fixed to it. Of course, additionally or alternatively to this, at least one force-locking element, such as a smooth pin, may also be used. In lieu of a pin, a velcro element, for instance, or another such positive-locking element may be used. Due to the configuration according to the invention, it is possible to use the mechanical connection of the liner in the distal region to the prosthesis socket without the known milking effect occurring. This effect is at least greatly reduced. It is thereby possible to distribute the tensile forces that are acting on the liner only in the vicinity of the positive-locking elements and that are exerted during the swing phase of a gait cycle, as evenly as possible in form of forces acting in the radial direction across the entire liner and thus across the amputation stump. The milking effect does not occur. As a result, this as homogeneous as possible distribution of forces, which is generally known from negative pressure connections, can be combined with the connection of the liner in the distal region to the prosthetic socket, said connection being more secure and deemed more reliable. In this case, a pneumatic seal against the surroundings is not necessary.

Preferably, the liner features at least one tension element at a distal end, such as a belt or a belt system, by means of which the liner can be pulled into a prosthetic socket. To this end, the respective tension element is pulled through a recess on the prosthetic socket that has been provided specifically for this purpose. The tension element can then be fixed on the outside of the prosthetic socket, for instance.

It is preferable if different holding mechanisms are provided, wherein an auxetic material is always used. This means that, for example, a negative pressure supply can be used in the distal region. To this end, the liner preferably has a sealing lip which seals a distal volume between the liner and the prosthetic socket, wherein said seal is airtight. The two-dimensional-auxetic material is preferably used in the proximal region of the liner.

It is beneficial if the auxetic material is embedded, preferably moulded, into the liner material, or applied to an outer side of the liner material. This renders the production of this liner especially simple.

Preferably, the auxetic material forms a separate layer, which is preferably connected to the liner material in a bonded and/or positive-locking manner. For instance, the layer can be produced in a separate process step, for example by way of a 3D print with a 3D printer, and then connected to the liner material. This may also occur following the production of the liner material, i.e. in particular following the hardening, cooling or curing of the liner material.

The auxetic material is preferably connected to the connecting element in such a way that the tensile and/or compressive forces can be transferred. The tensile and/or compressive forces which occur during use of the prosthesis can thus be transferred via the connecting element. They then have the effect in the auxetic material described above.

Preferably the liner has an anti-slip coating on an inner side, said coating lying closely on the skin of the wearer when the liner is mounted.

The auxetic material is preferably formed of a textile or designed to be a panel material. The auxetic property can preferably be achieved, for instance, by removing unnecessary elements and/or parts and/or areas of the panel-shaped material, especially by cutting or punching. Cast or laser-cut auxetic materials can also be used. These panel-shaped auxetic materials can then be configured such that they can be set to the respectively required size and shape, and used for the liner.

It is beneficial if the auxetic material is or can be produced by a 3D printer. The auxetic material may be a plastic that can be brought into certain structures that have two-dimensional-auxetic properties. It is practical for this to be achieved using a 3D printer. In this case, the two-dimensional-auxetic material can be easily adjusted to the desired shape, which is determined by the size and/or design of the liner, for instance. The material can be produced individually, so that an optimal fit and an optimal connection between liner and skin of the wearer can be achieved.

The auxetic material can preferably be imprinted onto the liner material.

Preferably, the auxetic material is part of a textile, preferably a knitted fabric, especially preferably a circular knitted fabric, which forms an outer layer of the liner. This renders the production of the liner even easier.

A liner according to the embodiments described here may be produced using an injection moulding procedure, for example, especially a so-called 2K procedure. This renders it possible, for example, to produce the auxetic material in a liner mould, in which the liner is produced, in a first injection moulding step. The liner material is subsequently cast in the same liner mould. Alternatively, the liner material, such as an elastomer material, can be pre-produced. The auxetic material can be cast or injected onto this liner material. Alternatively, the auxetic material can be pre-produced and laid in the liner mould as an inlay element before the liner material is cast or injected.

During the swing phase of a step, the liner lies on the socket and can ensure that the stump volume remains constant. This can also improve the flow of blood in the amputation stump.

BRIEF DESCRIPTION OF THE DRAWINGS

In the following, an example of an embodiment of the present invention will be explained by way of the attached drawings: They show.

DETAILED DESCRIPTION

Figure 1:
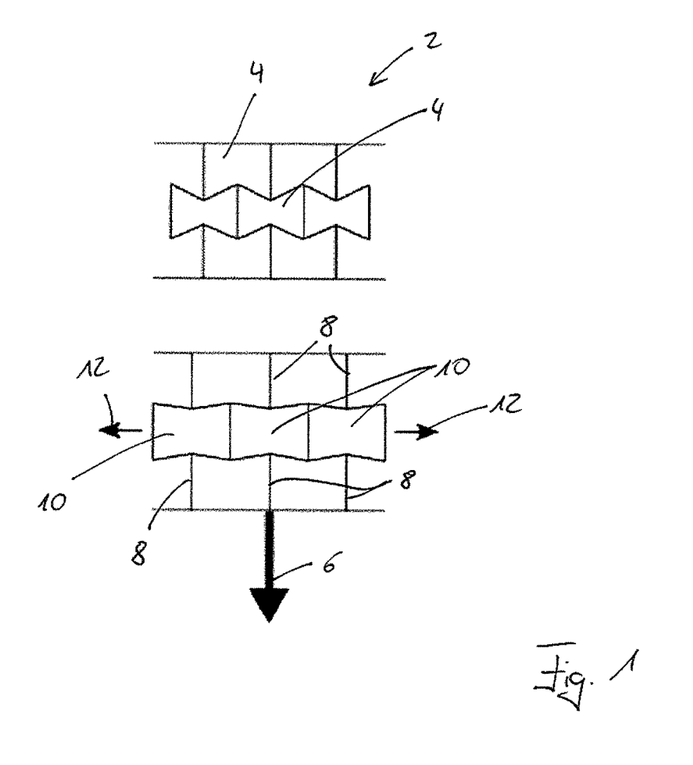
FIG. 1—the schematic functioning of an exemplary two-dimensional-auxetic material, FIG. 2—the schematic depiction of a liner according to a first example of an embodiment of the present invention, FIG. 3—the functioning of a liner according to an example of an embodiment of the present invention, FIG. 4—the schematic depiction of a further auxetic material, FIG. 5—the functioning of a liner according to another example of an embodiment.

FIG. 1 shows a two-dimensional-auxetic material 2. The upper section shows said material in a slack, unloaded state. It features a special shape with different meshes or cells 4. Here, the individual borders of these cells 4 may be made of a conventional plastic, which can be printed by a 3D printer, for example. The special geometric form of the different cells 4 gives the auxetic material 2 a negative Poission's ratio. This is depicted in the lower part of FIG. 1. A tensile force is exerted along the first arrow 6, said force being transferred via the vertically depicted cell walls 8 onto expandable cells 10. As a comparison with the upper part of FIG. 1 clearly shows, the respective lateral walls are pulled apart, also resulting in an increase in their length in the transverse direction, i.e. from left to right in FIG. 1. As a result, the auxetic material 2 not only becomes larger in the direction of the first arrow 6 and extends, but it also expands in a perpendicular direction, which is depicted by the second arrow 12. A thickening or expansion in a third direction, wherein said direction is perpendicular to the two first directions and would be perpendicular to the drawing plane in FIG. 1, does not occur.

Figure 2:
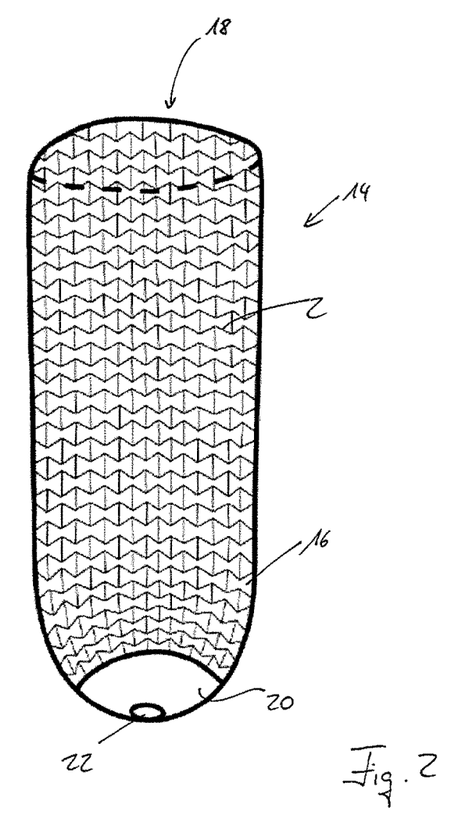

FIG. 2 shows a liner 14 that is made of a liner material 16 and comprises the two-dimensional-auxetic material 2. The liner 14 has a proximal opening 18 for accommodating an amputation stump and a distal end 20, which features a positive-locking element 22 in the example of an embodiment shown. A cap or cup may be also be arranged in the vicinity of the distal end 20, by way of which the tensile forces that are transferred via the positive-locking element 22 when the liner is mounted can be safely transferred, wherein said liner is connected to a prosthetic socket, not depicted.

Figure 3:
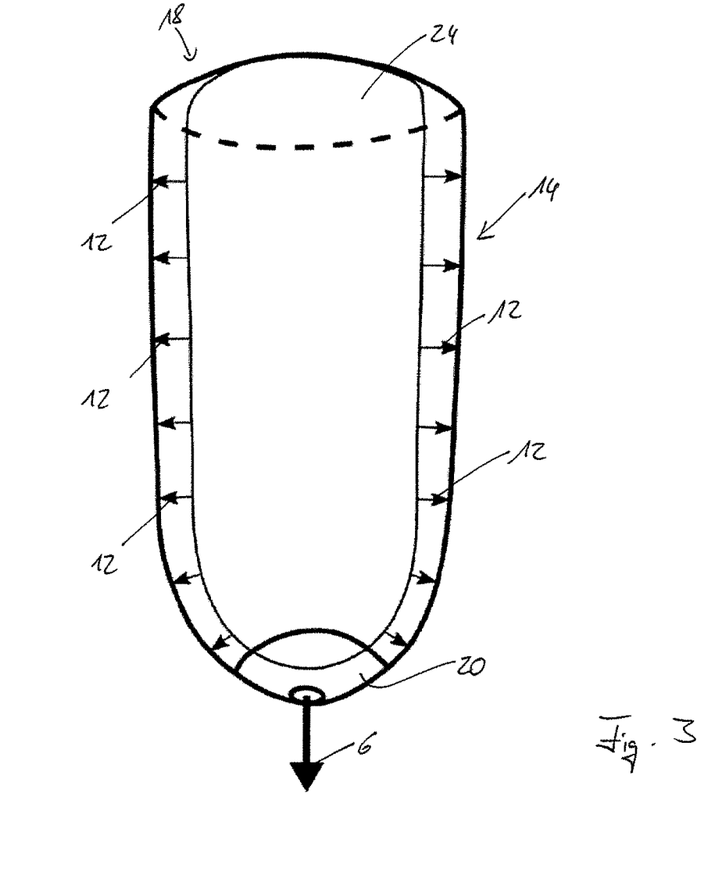

FIG. 3 shows the schematic depiction of the liner 14, in which an amputation stump 24 is situated. The proximal opening 18 and the distal end 20 can be recognized, wherein a tensile force is applied along the first arrow 6 in the example of an embodiment shown. For reasons of clarity, a depiction of the auxetic material 2 has not been provided. However, the liner 14 in the example of an embodiment shown in FIG. 3 comprises this two-dimensional-auxetic material 2.

The tensile force that is applied to the distal end 20 along the first arrow 6 causes an extension of the liner 14 along its longitudinal direction, which extends from the proximal opening 18 to the distal end 20. Since the material is two-dimensional-auxetic, this extension along the longitudinal direction also causes an expansion of the liner and thus an increase in the diameter of the liner 14. This is shown via the second arrow 12. A tensile force is thus transferred to the amputation stump 24, which ideally acts on the entire surface of the amputation stump 24, said surface coming into contact with an inner side of the liner 14. As a result, on the one hand the tensile force is evenly distributed across the liner 14 and thus also the amputation stump 24 in the direction of the first arrow 6; on the other hand, it no longer only acts along the longitudinal direction but also ensures that a force acts in the radial direction along the second arrow 12. In every gait cycle, a corresponding force is applied during the swing phase, resulting in said force countering a decrease in volume of the amputation stump 24.

Figure 4:
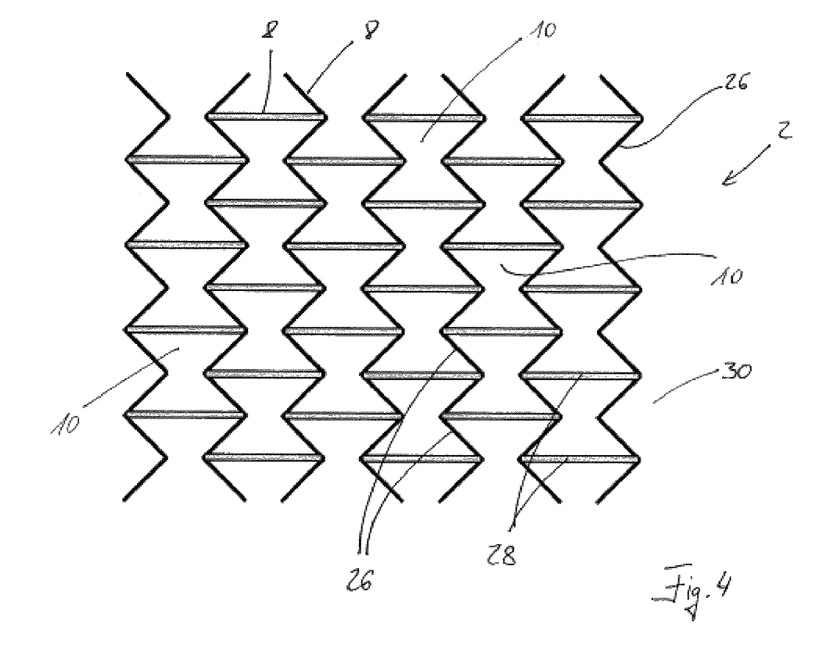

FIG. 4 shows a further auxetic material 2 which features the structure shown in FIG. 1. It has expandable cells 10, which are restricted by cell walls 8.

The cell walls 8 are walls 26 that are arranged in a zigzag pattern and are tension-stable, between which pressure-stable reinforcement elements 28 are arranged, which border the expandable cells 10. The tension-stable walls 26 and the pressure-stable reinforcement elements 28 ensure the auxetic property of the auxetic material 2. They are embedded in a fabric 30, which is bi-directionally elastic. Here, the tension-stable walls 26 and the pressure-stable reinforcement elements 28 may be applied to the material, for instance glued, coated or by way of vapor deposition, or they may be integrated into the fabric 30.

Figure 5:
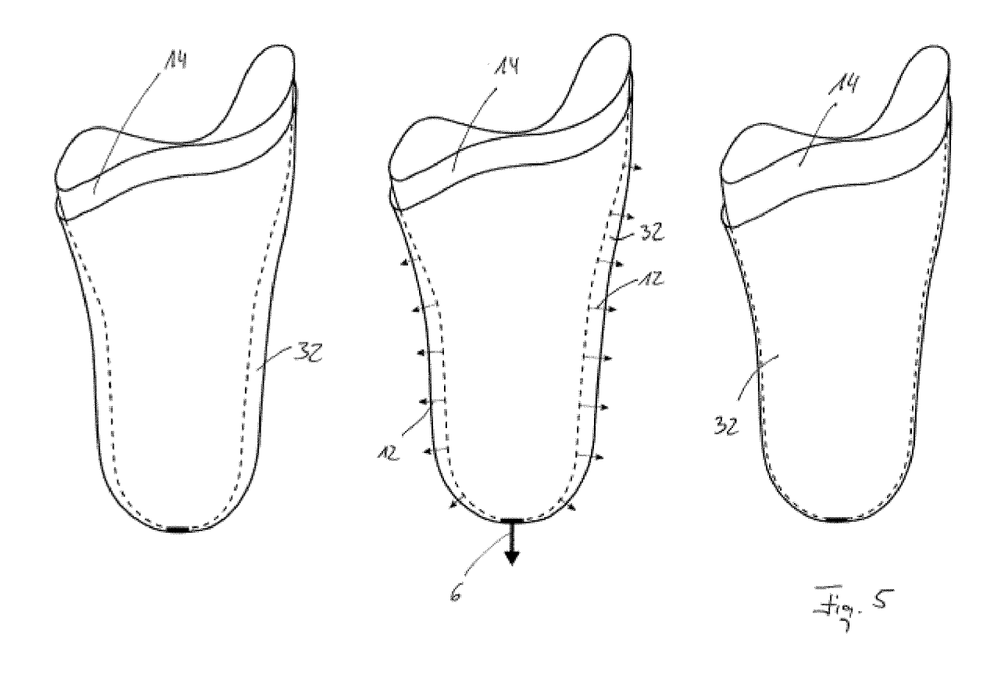

FIG. 5 shows a liner 14 in a prosthetic socket 32. By way of a dashed line, the liner 14 is shown at a point at which it cannot be seen through the prosthetic socket 32.

The left-hand image in FIG. 5 shows the unloaded state. Conversely, in the central image, a force is acting on the liner 14 along the first arrow 6. This force may occur, for example, during the swing phase of a step. Due to the auxetic properties of the material of the liner 14, the liner expands along the directions shown by the second arrows 12. This results in the situation shown in the right-hand image in FIG. 5, in which the liner 14 and the amputation socket inside it, not depicted, optimally fill the prosthetic socket 32.

I claim:

1. A liner for a prosthesis, comprising:
    a liner material;
    a proximal opening for accommodating an amputation stump;
    a distal end;
    a longitudinal direction, which extends from the proximal opening to the distal end;
    a two-dimensional-auxetic material, which is arranged such that an extension of the liner in the longitudinal direction leads to an expansion of only one other dimension of the liner.

2. The liner according to claim 1, wherein the liner has a fixing element with which the liner can be introduced into a recess of the prosthetic socket and thus fixed to it.

3. The liner according to claim 1, wherein the auxetic material is embedded in the liner material or applied to an outer side of the liner material.

4. The liner according to claim 1, wherein the auxetic material forms a separate layer, which is connected to the liner material via a force-locking connection.

5. The liner according to claim 2, wherein the auxetic material is connected to the fixing element such that at least one of tensile and compressive forces can be transferred.

6. The liner according to claim 1, wherein the liner further comprises an anti-slip coating on an inner side, the coating configured to contact skin of the wearer when the liner is mounted.

7. The liner according to claim 1, wherein the auxetic material can be or is produced by a 313 printer.

8. The liner according to claim 7, wherein the auxetic material is imprinted on the liner material.

9. The liner according to claim 1, wherein the auxctic material is part of a textile which forms an outer layer of the liner.

10. A liner for a prosthesis, comprising:
    a liner material;
    an internal cavity;
    a proximal opening to receive an amputation stump into the internal cavity;

a closed distal end;

a longitudinal dimension extending from the proximal opening to the distal end;

a two-dimensional-auxetic material arranged such that an extension of the liner in the longitudinal dimension leads to an expansion of only one other dimension of the liner.

11. The liner according to claim 10, wherein the liner has a fixing element with which the liner is secured to the prosthesis.

12. The liner according to claim 10, wherein the auxetic material is embedded in the liner material or applied to an outer side of the liner material.

13. The liner according to claim 10, wherein the auxetic material forms a separate layer, which is connected to the liner material via a force-locking connection.

14. The liner according to claim 11, wherein the auxetic material is connected to the fixing element such that at least one of tensile and compressive forces can be transferred.

15. The liner according to claim 10, wherein the liner further comprises an anti-slip coating on an inner side, the coating configured to contact skin of the wearer when the liner is mounted to the amputation stump.

16. The liner according to claim 10, wherein the auxetic material is produced by a 3D printer.

17. The liner according to claim 16, wherein the auxetic material is imprinted on the liner material.

18. The liner according to claim 10, wherein the auxetic material is part of a textile which forms an outer layer of the liner.

* * * * *